US012747216B2

(12) United States Patent
Jung et al.

(10) Patent No.: US 12,747,216 B2
(45) Date of Patent: Sep. 29, 2026

(54) COMPOUND, METHOD FOR PREPARING SAME, AND SINGLE MOLECULE, OLIGOMER AND POLYMER DERIVED FROM SAME

(71) Applicant: LG CHEM, LTD., Seoul (KR)

(72) Inventors: Jihye Jung, Daejeon (KR); Beomsu Park, Daejeon (KR); Hyun Cheol Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 311 days.

(21) Appl. No.: 18/706,712

(22) PCT Filed: Jan. 17, 2023

(86) PCT No.: PCT/KR2023/000792
§ 371 (c)(1),
(2) Date: May 1, 2024

(87) PCT Pub. No.: WO2023/136702
PCT Pub. Date: Jul. 20, 2023

(65) Prior Publication Data

US 2025/0051291 A1 Feb. 13, 2025

(30) Foreign Application Priority Data

Jan. 17, 2022 (KR) ........................ 10-2022-0006320

(51) Int. Cl.
*C07D 251/34* (2006.01)
*C08G 73/06* (2006.01)

(52) U.S. Cl.
CPC ....... *C07D 251/34* (2013.01); *C08G 73/0655* (2013.01)

(58) Field of Classification Search
CPC .......................... C07D 251/34; C08G 73/0655
See application file for complete search history.

(56) References Cited

U.S. PATENT DOCUMENTS 5,247,036 A 9/1993 Krueger
2016/0032039 A1 2/2016 Shimizu et al.
2020/0165277 A1 5/2020 Kubodera et al.
2020/0389973 A1 12/2020 Uchida
2021/0230327 A1 7/2021 Chernysheva et al.
2022/0204690 A1 6/2022 Nose

FOREIGN PATENT DOCUMENTS

CN 107739346 B 9/2020
EP 0937717 A1 8/1999
EP 3498756 A1 6/2019
EP 3780226 A1 2/2021
JP S55-160770 A 12/1980
JP 05-0086135 A 4/1993
JP 05-117247 A 5/1993
JP 2005-047880 A 2/2005
JP 6756990 B2 9/2020
JP 2021-0175807 A 11/2021
KR 2015-0140636 A 12/2015
KR 2020-0020682 A 2/2020
KR 2020-0110424 A 9/2020

OTHER PUBLICATIONS

Gryaznova, T. V., et al. "Palladium nanoparticles-polypyrrole composite as effective catalyst for fluoroalkylation of alkenes." Catalysis Letters 148.10 (2018): 3119-3125. (Year: 2018).*
European Search Report issued for European Patent Application No. 23740545.1 on Nov. 13, 2024, 10 pages.
International Search Report issued for International Application No. PCT/KR2023/000792 on May 9, 2023, 4 pages.
Yajima et al., "Photoinduced addition and addition-elimination reactions of perfluoroalkyl iodides to electron-deficient olefins" Tetrahedron 68 (2012) 6856-6861.
Gryaznova, et al., "Palladium Nanoparticles-Polypyrrole Composite as Effective Catalyst for Fluoroalkylation of Alkenes" Catalysis letters, 2018, 148:3119-3125.
Zang, et al., "Synthesis of Perfluoroalkyl Siloxane with C=C and C—C Bridged Groups Through Single Electron Transfer Reaction" Phosphorus, sulfur, and silicon and the related elements, 2015, 190:1035-1044.

* cited by examiner

*Primary Examiner* — Kamal A Saeed
(74) *Attorney, Agent, or Firm* — ROTHWELL, FIGG, ERNST & MANBECK, P.C.

(57) ABSTRACT

The present specification relates to a compound, a method for preparing the same, and a single molecule, an oligomer and a polymer derived from the compound.

6 Claims, 1 Drawing Sheet

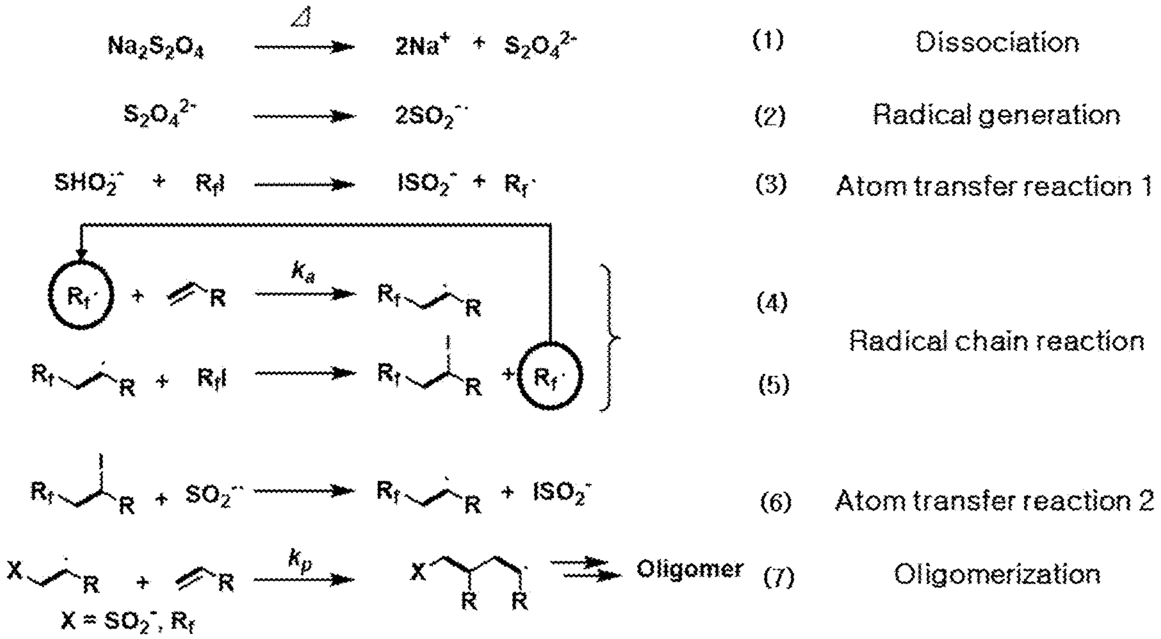
(1) Dissociation
(2) Radical generation
(3) Atom transfer reaction 1
(4)
(5) Radical chain reaction
(6) Atom transfer reaction 2
(7) Oligomerization

COMPOUND, METHOD FOR PREPARING SAME, AND SINGLE MOLECULE, OLIGOMER AND POLYMER DERIVED FROM SAME

TECHNICAL FIELD

This application is a 35 U.S.C. § 371 National Phase Entry Application from PCT/KR2023/000792, filed on Jan. 17, 2023, which claims priority to and the benefit of Korean Patent Application No. 10-2022-0006320 filed in the Korean Intellectual Property Office on Jan. 17, 2022, the entire contents of which are incorporated herein by reference.

The present specification relates to a compound, a method for preparing the same, and a single molecule, an oligomer and a polymer derived from the compound.

BACKGROUND

Triallyl isocyanurate is useful as a cross-linking agent having excellent heat resistance and chemical resistance, and is expected to be used in a wide range of fields such as electronic materials, liquid crystals, semiconductors, and solar cells. For example, in printed circuit boards, that is, plate-like or film-like parts that constitute electronic circuits by fixing a large number of electronic parts such as integrated circuits, resistors, and condensers to a surface thereof and connecting the parts through wiring, triallyl isocyanurate is used as a sealing material for preventing penetration of materials such as liquids or gases into the parts.

However, triallyl isocyanurate has high relative permittivity and high dissipation factor, so that research has been continuously conducted to reduce them.

SUMMARY

Technical Problem

The present specification provides a compound, a method for preparing the same, and a single molecule and an oligomer derived from the compound.

Technical Solution

An exemplary embodiment of the present specification provides a compound of the following Chemical Formula 1.

[Chemical Formula 1]

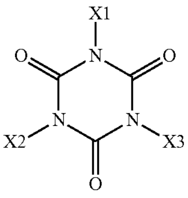

In Chemical Formula 1, at least one of X1 to X3 is

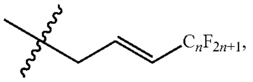

and the others are an allyl group, n is an integer from 1 to 20, and

is a moiety bonded to Chemical Formula 1.

An exemplary embodiment of the present specification provides a method for preparing a compound of the following Chemical Formula 1, the method including: (s1) putting triallyl isocyanurate, $C_nF_{2n+1}X4$, a first base, and a first solvent into a container and stirring the resulting mixture under nitrogen gas; (s2) adding a radical initiator thereto and stirring the resulting mixture; and (s3) adding a second solvent and a second base thereto.

[Chemical Formula 1]

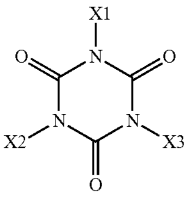

In Step (s1) and Chemical Formula 1, at least one of X1 to X3 is

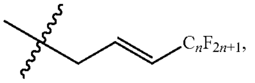

and the others are an allyl group, n is an integer from 1 to 20,

is a moiety bonded to Chemical Formula 1, and

X4 is a halogen group.

An exemplary embodiment of the present specification provides a mixture including two or more of the compounds.

Another exemplary embodiment of the present specification provides a single molecule derived from the compound.

Further, still another exemplary embodiment of the present specification provides an oligomer including a monomer derived from the compound.

Yet another exemplary embodiment of the present specification provides a polymer including a monomer derived from the compound.

Advantageous Effects

The compound according to an exemplary embodiment of the present specification, and the single molecule, the oligomer and the polymer derived therefrom include a good release group and a structure capable of being cross-linked, so that various derivatives can be prepared.

The compound according to an exemplary embodiment of the present specification can be used as a polyfunctional monomer to exhibit the effects of achieving low refractive index, low relative permittivity, low surface energy and low dissipation factor.

In the method for preparing a compound according to an exemplary embodiment of the present specification, the reaction is performed under mild conditions with minimal side reactions, so that the yield of the compound of Chemical Formula 1, which is a target compound, is increased.

BRIEF DESCRIPTION OF DRAWINGS

FIG. 1 is a view describing the mechanism of the method for preparing the compound of Chemical Formula 1.

DETAILED DESCRIPTION

Hereinafter, the present specification will be described in more detail.

An exemplary embodiment of the present specification provides a compound of the following Chemical Formula 1.

[Chemical Formula 1]

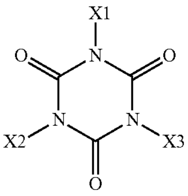

In Chemical Formula 1, at least one of X1 to X3 is

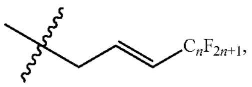

and the others are an allyl group, n is an integer from 1 to 20, and

is a moiety bonded to Chemical Formula 1.

The compound of Chemical Formula 1 according to an exemplary embodiment of the present specification includes a perfluoroalkyl group including fluorine having the effects of achieving low refractive index, low relative permittivity, and low dissipation factor, and a double bond that reduces the degree of freedom, and is used as a polyfunctional monomer as a triallyl isocyanurate derivative that serves as a cross-linking agent, so that it is possible to exhibit the effects of achieving low refractive index, low relative permittivity, low surface energy and low dissipation factor.

According to an exemplary embodiment of the present specification, any one of X1 to X3 is,

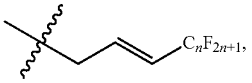

and the others are an allyl group.

According to an exemplary embodiment of the present specification, any two of X1 to X3 are

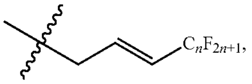

and the other is an allyl group.

According to an exemplary embodiment of the present specification, X1 to X3 are each

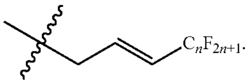

According to an exemplary embodiment of the present specification, n is an integer from 4 to 12.

According to an exemplary embodiment of the present specification, n is 4, 6 or 8.

According to an exemplary embodiment of the present specification, the

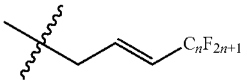

is any one of the following structures.

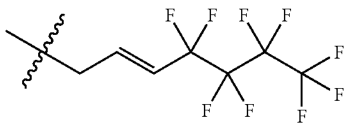

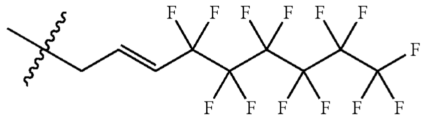

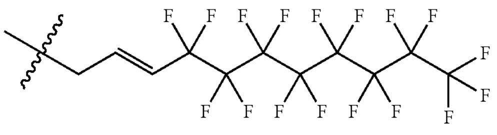

According to an exemplary embodiment of the present specification, when n of the

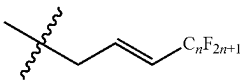

is within the above range, compounds with various molecular weights may be prepared because the chain length of a perfluoroalkyl group is easily adjusted. In addition, when a perfluoroalkyl group is included, it is possible to exhibit effects of achieving low refractive index, low relative permittivity, low surface energy and low dissipation factor.

According to an exemplary embodiment of the present specification, Chemical Formula 1 is any one selected from the following compounds.

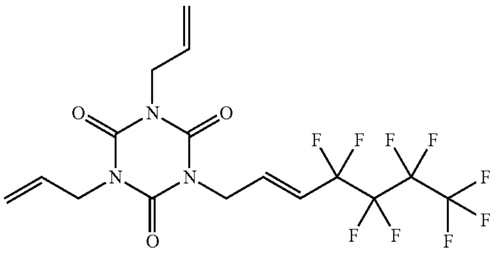

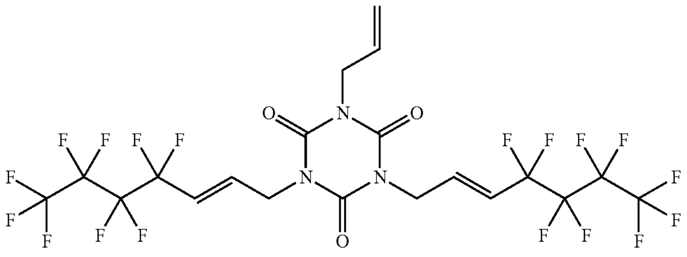

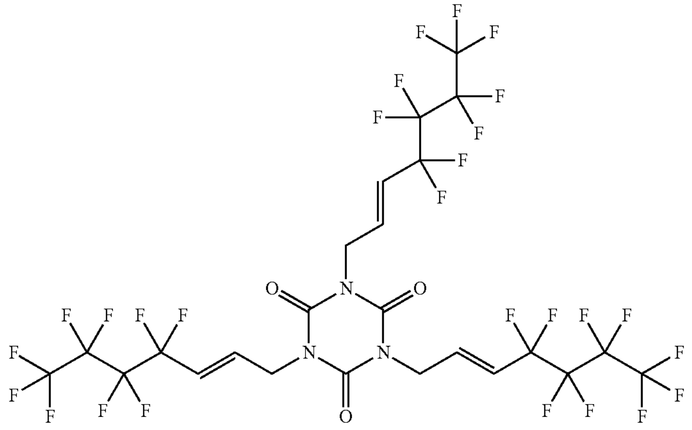

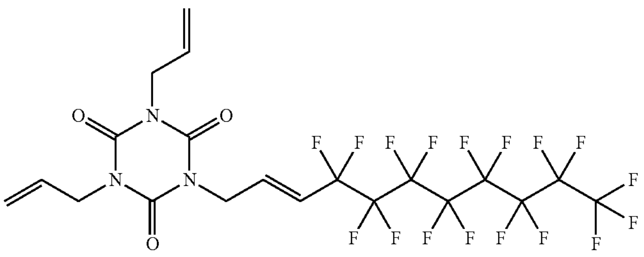

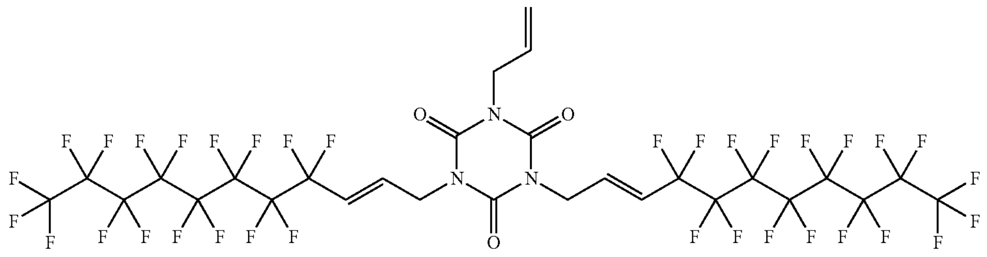

-continued
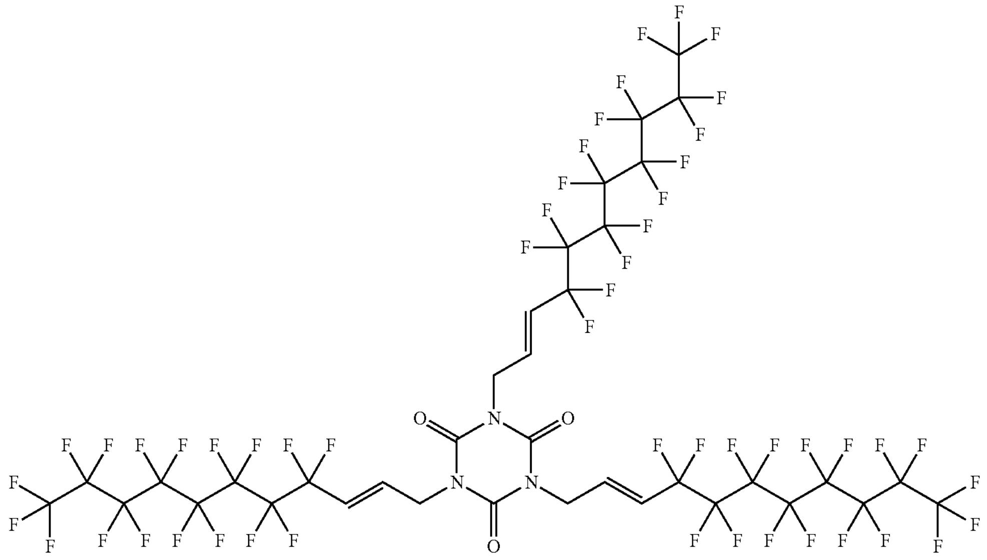
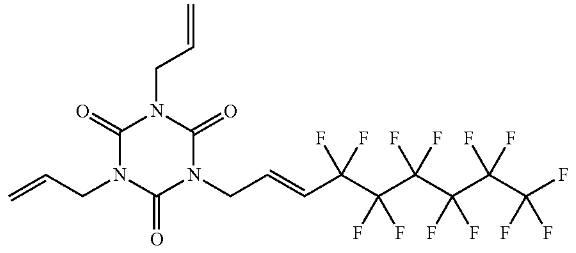
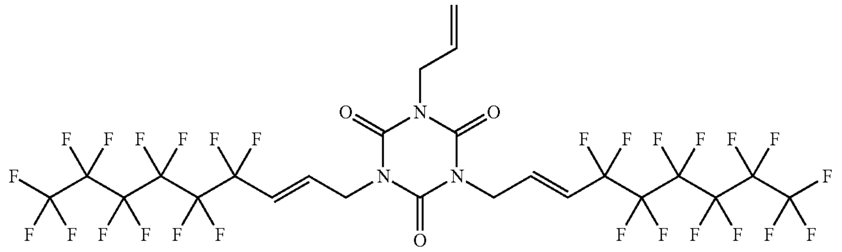
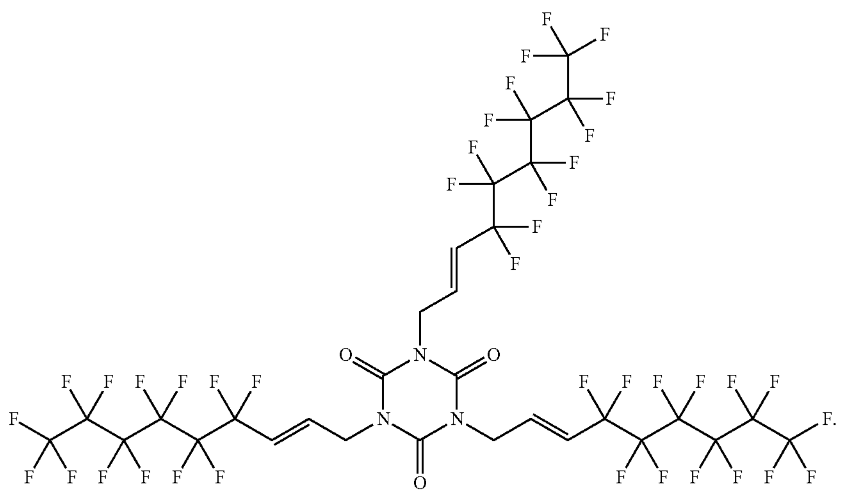

An exemplary embodiment of the present specification provides a method for preparing a compound of the following Chemical Formula 1, the method including: (s1) putting triallyl isocyanurate, $C_nF_{2n+1}X4$, a first base, and a first solvent into a container and stirring the resulting mixture under nitrogen gas; (s2) adding a radical initiator thereto and stirring the resulting mixture; and (s3) adding a second solvent and a second base thereto.

[Chemical Formula 1]

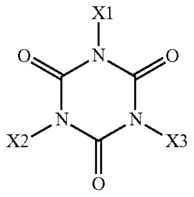

In Step (s1) and Chemical Formula 1, at least one of X1 to X3 is,

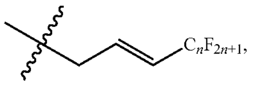

and the others are an allyl group, n is an integer from 1 to 20,

is a moiety bonded to Chemical Formula 1, and

X4 is a halogen group.

According to an exemplary embodiment of the present specification, X4 is an iodine group (—I).

According to an exemplary embodiment of the present specification, the reaction temperature in Step (s1) is 0° C. to room temperature. When the above reaction is performed within the above reaction temperature range, the reaction conditions are not tricky but mild, and side reactions that appear as the temperature rises are suppressed, so that the yield of the compound of Chemical Formula 1, which is a final target, is increased. In addition, various temperature ranges may be set according to the range of n and the molecular weight of the compound of Chemical Formula 1 in Step (s1).

In the present specification, room temperature means 20±5° C. under atmospheric pressure.

The first base according to an exemplary embodiment of the present specification is a non-nucleophilic base.

The first base according to an exemplary embodiment of the present specification may be potassium carbonate ($K_2CO_3$), sodium hydrogen carbonate ($NaHCO_3$), potassium hydrogen carbonate ($KHCO_3$), 1,8-diazabicyclo[5,4,0] undec-7-ene (DBU) or any mixture thereof, but is not limited thereto, and a salt used in the related art may be used.

According to an exemplary embodiment of the present specification, the first solvent is an organic solvent.

According to an exemplary embodiment of the present specification, the first solvent is selected among hexane, heptane, toluene, benzene, acetonitrile, dichloromethane (methylene chloride), dichloroethane, trichloroethane, chloroform, dichloroform, nitromethane, dibromomethane, cyclopentanone, cyclohexanone, fluorobenzene, bromobenzene, chlorobenzene, xylene, mesitylene, ethylacetate or any mixture thereof, but is not limited thereto, and an organic solvent used in the related art may be used.

According to an exemplary embodiment of the present specification, the radical initiator is a water-soluble initiator.

According to an exemplary embodiment of the present specification, the radical initiator is any one of potassium persulfate (KPS), ammonium persulfate (APS), potassium hydrosulfite, sodium hydrosulfite, sodium persulfate, or hydrogen peroxide.

According to an exemplary embodiment of the present specification, the reaction temperature in Step (s2) is 0° C. or higher. Specifically, the reaction temperature in Step (s2) is 0° C.

When Step (s2) is performed at the above reaction temperature, side reactions are suppressed, so that the yield of the compound of Chemical Formula 1, which is a final target, is increased.

According to an exemplary embodiment of the present specification, the second solvent is an organic solvent.

According to an exemplary embodiment of the present specification, the second solvent is selected among hexane, heptane, toluene, benzene, acetonitrile, dichloromethane (methylene chloride), dichloroethane, trichloroethane, chloroform, dichloroform, nitromethane, dibromomethane, cyclopentanone, cyclohexanone, fluorobenzene, bromobenzene, chlorobenzene, xylene, mesitylene, ethylacetate or any mixture thereof, but is not limited thereto, and an organic solvent used in the related art may be used.

According to an exemplary embodiment of the present specification, the second base is a non-nucleophilic base.

The second base according to an exemplary embodiment of the present specification may be potassium carbonate ($K_2CO_3$), sodium hydrogen carbonate ($NaHCO_3$), potassium hydrogen carbonate ($KHCO_3$), 1,8-diazabicyclo[5,4,0] undec-7-ene (DBU) or any mixture thereof, but is not limited thereto, and a salt used in the related art may be used.

According to an exemplary embodiment of the present specification, the adding of the second base in Step (s3) may be performed by dropwise addition, dropwise dropping, or a method used in the related art.

According to an exemplary embodiment of the present specification, the reaction temperature in Step (s3) is 0° C. to room temperature. When the above reaction is performed within the above reaction temperature range, the reaction conditions are not tricky but mild, and side reactions that appear as the temperature rises are suppressed, so that the yield of the compound of Chemical Formula 1, which is a final target, is increased. In addition, various temperature ranges may be set according to the range of n and the molecular weight of the compound of Chemical Formula 1 in Step (s3).

The mechanism of the preparation method according to an exemplary embodiment of the present specification is described in the following FIG. 1. (1) The radical initiator is dissociated under basic conditions, (2) radicals are generated, and (3) the first atom transfer reaction occurs. The hydrogen of the initiator is dissociated in (3) and bonded to a halogen group (an iodine group) bonded to perfluoroalkyl, and the perfluoroalkyl becomes a radical. Thereafter, by the radical chain reaction of (4) and (5), (4) the radicalized perfluoroalkyl group and the allyl group of the triallyl isocyanurate are bonded to form a radical, (5) the halogen group (the iodine group) bonded to the perfluoroalkyl is bonded to the radical to produce an intermediate compound in which the halogen group (the iodine group) is bonded, and (6) the halogen group is dissociated in the intermediate compound by the second atom transfer reaction, and a removal reaction occurs to produce a compound of Chemical Formula 1 including a perfluoroalkyl group including a double bond. Additionally, (7) oligomerization may occur due to the radicals generated by the reaction of (6).

In FIG. 1, $K_a$ is the addition rate constant of radical to substrate ($R_f$), and $K_p$ is the oligomerization rate constant of substrate.

According to an exemplary embodiment of the present specification, a step of obtaining an intermediate compound after Step (s2) and a step of obtaining the compound of Chemical Formula 1 after Step (s3) are further included.

The obtaining of the compound of Chemical Formula 1a according to an exemplary embodiment of the present specification includes:

(s41) a quench and layer separation step;

(s42) a drying step;

(s43) a filtration step;

(s44) a concentration step; and (s45) an obtaining step.

According to an exemplary embodiment of the present specification, Step (s41) (quench and layer separation step) is a step of terminating the reaction by adding a reaction termination material, and separating the layers.

According to an exemplary embodiment of the present specification, as the reaction termination material of Step (s41), distilled water, an aqueous ammonium chloride solution, an aqueous sodium hydrogen carbonate solution, an aqueous KF (saturated) solution, an aqueous HCl solution, an aqueous NaCl (saturated) solution, chloroform, dichloromethane, ethyl acetate, and the like may be used, but the reaction termination material is not limited thereto. Preferably, as the reaction termination material, an aqueous ammonium chloride solution, an aqueous sodium hydrogen carbonate solution, an aqueous NaCl solution, and ethyl acetate are used.

In Step (s41), the order in which the reaction termination and layer separation are performed is not limited to a specific order. As an exemplary embodiment, reaction termination and layer separation may be simultaneously performed, and as another exemplary embodiment, the reaction is terminated by adding a reaction termination material, and then layers may be separated. However, the progression order is not limited to the above-described example.

Since the radical initiator remaining after Step (s2) is water-soluble, the radical initiator may be dissolved in water and removed in Step (s41).

According to an exemplary embodiment of the present specification, Step (s42) (drying step) is performed by adding a desiccant to any one layer of the material layer-separated in Step (s41). For example, when chloroform exemplified above is used as the reaction termination material, Step (s42) is performed by adding a desiccant to a chloroform layer which is a lower layer, that is, an organic layer.

Examples of the desiccant include magnesium sulfate, sodium sulfate, and the like, but are not limited thereto. According to a preferred exemplary embodiment, the desiccant is magnesium sulfate.

In the present specification, the desiccant is added in a sufficient amount required for typical drying in the art.

According to an exemplary embodiment of the present specification, Step (s43)(filtration step) may be performed by a method known in the art. As a representative example, it is possible to use a method of inhaling air using an inhaler and filtering impurities including a desiccant, and the like, which are separated from a target product with a filter, or a method of removing other impurities using a solvent that does not dissolve a target product, but dissolves other impurities by utilizing the difference in solubility in a specific solvent.

According to an exemplary embodiment of the present specification, Step (s44)(concentration step) may be performed by a method known in the art. The step may be performed by evaporating the solvent using a vacuum rotary evaporator as a representative example, but the representative example is not limited thereto.

According to an exemplary embodiment of the present specification, additional filtration and drying steps may be added after Step (s44).

It is possible to include a drying step before the obtaining step (s45), and the drying step is a step of drying the intermediate compound, or the compound of Chemical Formula 1. The drying step is different from Step (s42) and may be performed by a method known in the art, representative examples thereof include vacuum oven drying, spray drying, flash drying, and the like, and preferably, the compound of Chemical Formula 1 may be dried by vacuum oven drying.

According to an exemplary embodiment of the present specification, Step (s45) (obtaining step) is a step of obtaining the intermediate compound, or the compound of Chemical Formula 1, which is concentrated (dried) in Step (s44).

According to an exemplary embodiment of the present specification, in the obtaining step, Steps (s42) to (s43) may be performed three or more times, if necessary.

According to an exemplary embodiment of the present specification, provided is a mixture including two or more of the compounds.

According to another exemplary embodiment of the present specification, two or more compounds included in the mixture are the same as or different from each other. That is, it means that the two or more compounds are the same as or different from each other while having the structure of Chemical Formula 1.

According to still another exemplary embodiment of the present specification, the mixture may further include a compound different from the compound of Chemical Formula 1.

According to an exemplary embodiment of the present specification, provided is a single molecule derived from the compound.

In the present specification, for example, the aforementioned "single molecule derived from the compound of Chemical Formula 1" may mean a single molecule in which the allyl group of the compound of Chemical Formula 1 forms a radical and an additional substituent is introduced, a single molecule in which an additional substituent is introduced using the halogen group of Chemical Formula 1 as an electron donor, or the compound of Chemical Formula 1 itself.

According to an exemplary embodiment of the present specification, provided is an oligomer including a monomer derived from the compound.

Those skilled in the art may understand the term "monomer" described in the present specification as a state in which a compound is polymerized to be linked to the main chain of the oligomer.

In the present specification, for example, the "monomer derived from the compound of Chemical Formula 1" is a repeating unit that constitutes the main chain in the polymer, and means that an allyl group of the compound of Chemical Formula 1 may form a radical to become a monomer, and a halogen group may be used as an electron donor to introduce a monomer or end group which makes up the main chain of other oligomers.

Furthermore, radicals generated by the release of the halogen group used as the electron donor may also react with other allyl group-containing oligomers or the above monomers.

The compound according to an exemplary embodiment of the present specification, and a single molecule and an oligomer derived therefrom include a good release group and a structure capable of being cross-linked, so that various derivatives can be prepared.

According to an exemplary embodiment of the present specification, provided is a polymer including a monomer derived from the compound.

Those skilled in the art will understand the term "monomer" described in the present specification as a state in which a compound is polymerized to be linked to the main chain of the polymer.

In the present specification, for example, the "monomer derived from the compound of Chemical Formula 1" is a repeating unit that constitutes the main chain in the polymer, and means that a vinyl group of the compound of Chemical Formula 1 may form a radical to become a monomer, and a monomer or end group which makes up the main chain of other polymers may be introduced.

According to an exemplary embodiment of the present specification, the polymer may further include an additional monomer, and the additional monomer is not limited.

According to an exemplary embodiment of the present specification, the polymer may be an alternating polymer or a random polymer, but is not limited thereto.

Further, in the present specification, even when a monomer included in the polymer is mentioned, the monomer is not limited to including only the mentioned monomer, and other monomers in addition to the aforementioned monomer may additionally be included as co-monomers within a range not departing from the object of the present invention. A compound according to an exemplary embodiment of the present specification, and a single molecule, an oligomer and a polymer derived therefrom are used as an electronic material, an organic insulating material, and/or a substrate material, but are not limited thereto.

MODE FOR INVENTION

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to explain the present specification more completely to a person with ordinary skill in the art.

Example 1

After 9.9 g of triallyl isocyanurate, 0.101 g of $NaHCO_3$ and 20.7 mL of nonafluoro-1-iodobutane were dissolved in 100 mL of water and 50 mL of acetonitrile in a 250 mL two-neck round-bottom flask and $N_2$ bubbling was performed at room temperature for 30 minutes, $Na_2S_2O_4$ was added thereto in a powder state, and then the resulting mixture was stirred at 0° C. for 17 hours. Thereafter, after the aqueous layer was extracted three times with 200 mL of chloroform, the organic layer was washed with water, and the washed organic layer was dried over 10 g of $MgSO_4$. Thereafter, filtration was performed and the solvent was evaporated to obtain 44 g of an intermediate compound from which perfluorobutyl iodide was derived.

After 14.38 g of the intermediate compound was dissolved in 13 mL of methylene chloride in a 100 mL two-neck round-bottom flask, 5.2 mL of 1,8-diazabicyclo[5,4,0]undec-7-ene (DBU) was added dropwise thereto over 1 minute. After 1 hour, 30 mL of 1N HCl was added, the resulting mixture was stirred for 30 minutes, then transferred to a separatory funnel and washed with 100 mL of HCl, 100 mL of a saturated $NaHCO_3$ solution and 200 mL of water, and then the organic layer was dried by adding 10 g of $MgSO_4$ thereto. Thereafter, filtration was performed and the solvent was evaporated to obtain 10 g of a final product. Among the final products measured by $^1$H-NMR, the mass ratios of Compounds 1-1 and 1-2 and Oligomer 1 and the weight average molecular weights measured by gel permeation chromatography (GPC) are shown in the following Table 1.

[Compound 1-1]

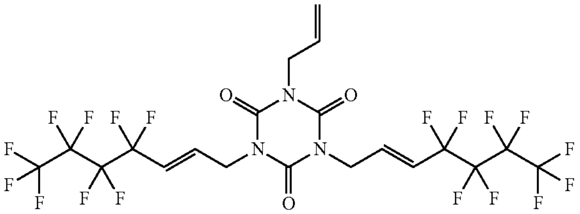

Molecular Weight: 685.31

[Compound 1-2]

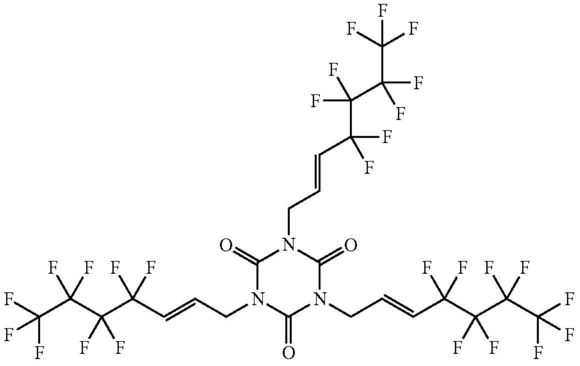

Molecular Weight: 903.33

TABLE 1

| Structure | Compound 1-1 | Compound 1-2 | Oligomer 1 | Molecular weight (by $^1$H-NMR) |
|---|---|---|---|---|
| Mass ratio (weight %) | 87 | 8 | 5 | 1300 |

Oligomer 1 of Example 1 is derived from any one or more of Compounds 1-1 and 1-2, and has a molecular weight that exceeds a molecular weight of Compound 1-2 that is the maximum unit as a single molecule.

Example 2

After 9.97 g of triallyl isocyanurate, 0.101 g of $NaHCO_3$ and 31.7 mL of heptadecafluoro-n-octyl iodide were dissolved in 100 mL of water and 40 mL of acetonitrile in a 250 mL two-neck round-bottom flask and $N_2$ bubbling was performed at 0° C. for 30 minutes, $Na_2S_2O_4$ was added thereto in a powder state, and then the resulting mixture was stirred at 0° C. for 17 hours. Thereafter, after the aqueous layer was extracted three times with 200 mL of chloroform, the organic layer was washed with water, and the washed organic layer was dried over 10 g of $MgSO_4$. Thereafter, filtration was performed and the solvent was evaporated to obtain 53 g of an intermediate product from which perfluorooctyl iodide was derived.

After 13.20 g of the intermediate compound was dissolved in 10 mL of methylene chloride in a 100 mL two-neck round-bottom flask, 3.2 mL of 1,8-diazabicyclo[5,4,0]undec-7-ene (DBU) was added dropwise thereto over 1 minute. After 1 hour, 30 mL of 1N HCl was added, the resulting mixture was stirred for 30 minutes, then transferred to a separatory funnel and washed with 100 mL of HCl, 100 mL of a saturated $NaHCO_3$ solution and 200 mL of water, and then the organic layer was dried by adding 10 g of $MgSO_4$ thereto. Thereafter, filtration was performed and the solvent was evaporated to obtain 10 g of a final product. Among the final products measured by $^1$H-NMR, the mass ratios of Compounds 2-1 and 2-2 and Oligomer 2 and the weight average molecular weights measured by gel permeation chromatography (GPC) are shown in the following Table 2.

[Compound 2-1]

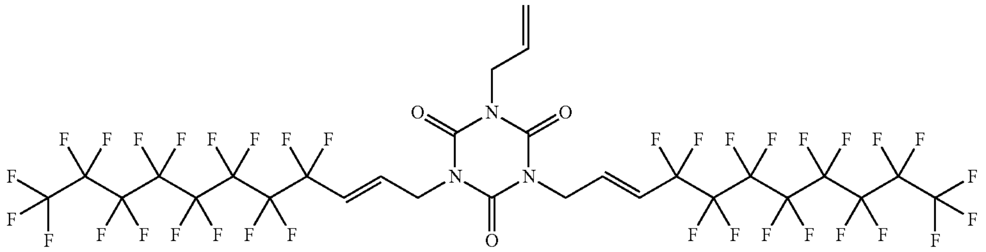

Exact Mass: 1085.04

[Compound 2-2]

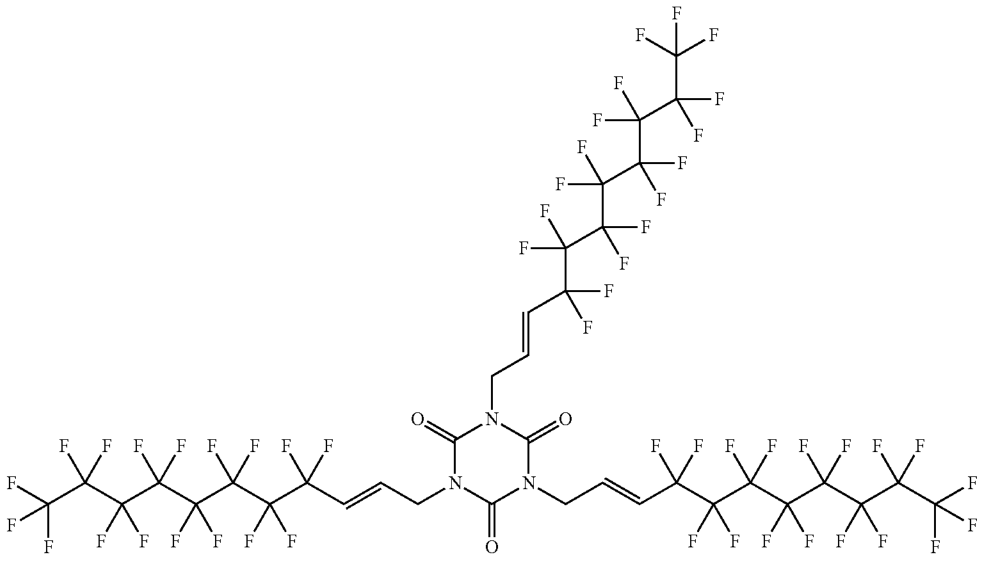

Exact Mass: 1503.01

TABLE 2

| Structure | Compound 2-1 | Compound 2-2 | Oligomer 2 | Molecular weight (by $^1$H-NMR) |
|---|---|---|---|---|
| Mass ratio (weight %) | 13 | 86 | 1 | 1100 |

Oligomer 2 of Example 2 is derived from any one or more of Compounds 2-1 and 2-2, and has a molecular weight that exceeds a molecular weight of Compound 2-2 that is the maximum unit as a single molecule.

Through Tables 1 and 2, the compound of Chemical Formula 1 includes a perfluoroalkyl group including fluorine having the effects of achieving low relative permittivity and low dissipation factor, and a double bond that reduces the degree of freedom, and is used as a polyfunctional monomer as a triallyl isocyanurate derivative that serves as a cross-linking agent, so that it is possible to exhibit the effects of achieving low refractive index, low relative permittivity, low surface energy (low surface tension) and low dissipation factor, and thus the compound of Chemical Formula 1 can be used as an electronic material, an organic insulating material, and/or a substrate material.

Evaluation Example: Measurement of Refractive Index and Surface Tension

The refractive indices of the final products prepared in Examples 1 and 2 and triallyl isocyanurate, which is the material of Comparative Example 1, were measured at 25° C. using RX-5000α (ATAGO Co., Ltd.).

Further, the surface tensions of the final products prepared in Examples 1 and 2 and triallyl isocyanurate, which is the material of Comparative Example 1, were measured using Tensiometer K11 (KRUSS GmbH). The surface tension was measured by making a 0.5 wt % Propylene glycol monomethyl ether acetate (PGMEA) solution at 27.8° C. to 28.1° C.

As the triallyl isocyanurate used in Comparative Example 1, a product manufactured by TCI Co., Ltd. was used.

TABLE 3

| Structure | Comparative Example 1 (Triallyl isocyanurate) | Evaluation Example 1 (Final product of Example 1) | Evaluation Example 2 (Final product of Example 2) |
|---|---|---|---|
| Refractive index | 1.51 | 1.40 | 1.36 |
| Surface tension (mN/m) | 25.6 | 25.0 | 21.2 |

In Table 3, it could be seen that the compound of the present specification has a lower refractive index and a lower surface tension than the triallyl isocyanurate of Comparative Example 1, which is a material in the related art. Therefore, the compound of the present specification may be used as an electronic material, an organic insulating material, and/or a substrate material.

Evaluation Example: Measurement of dielectric characteristics A coating composition was prepared by mixing the triallyl isocyanurate of Comparative Example 1 with OPE-2st (Mitsubishi Gas Chemical Company, Inc.) and a solvent such as toluene. A copper (Cu) foil was coated with the prepared coating composition and dried. After the dried film was vacuum-pressed at 225° C., dielectric characteristics were measured. The measured relative permittivity (Dk) value was 2.60.

A coating composition was prepared by mixing the final products of Examples 1 and 2 at a ratio of 1:1, instead of the triallyl isocyanurate of Comparative Example 1, and the dielectric characteristics were measured in the same manner. As a result, it was confirmed that the relative permittivity (Dk) value was lowered to 2.525.

Through the above results, the compound of Chemical Formula 1 may be used to lower the permittivity when the compound is prepared as a substrate material composition and applied to a copper clad laminate (CCL) or the like.

The invention claimed is:

1. A compound of Chemical Formula 1:

[Chemical Formula 1]

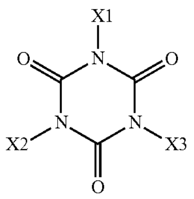

wherein, at least one of X1 to X3 is

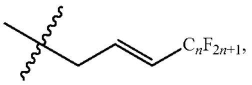

and the others are an allyl group, and n is an integer from 1 to 20.

2. The compound of claim 1, wherein n is 4 to 12.

3. The compound of claim 1, wherein the

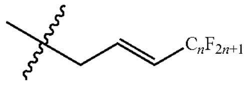

is any one of the following structures:

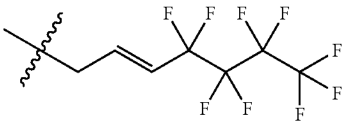

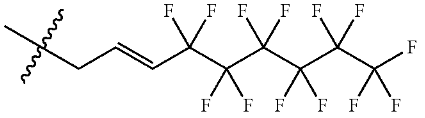

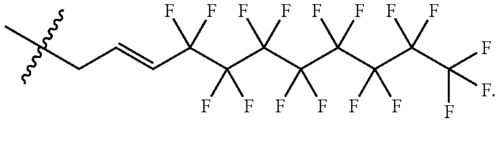

4. The compound of claim 1, wherein the Chemical Formula 1 is any one selected from the following compounds:
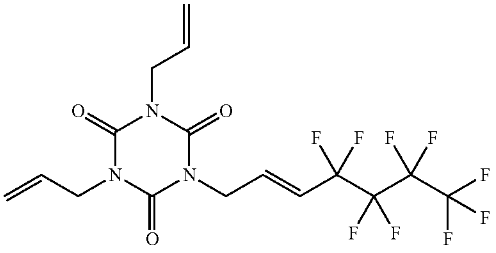
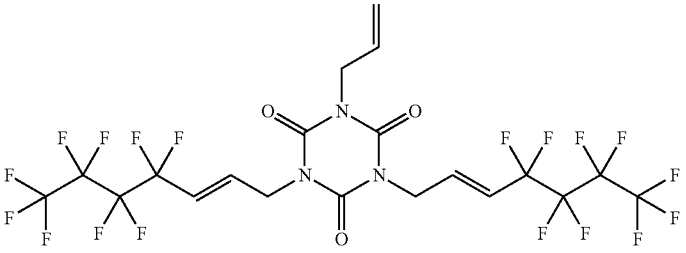
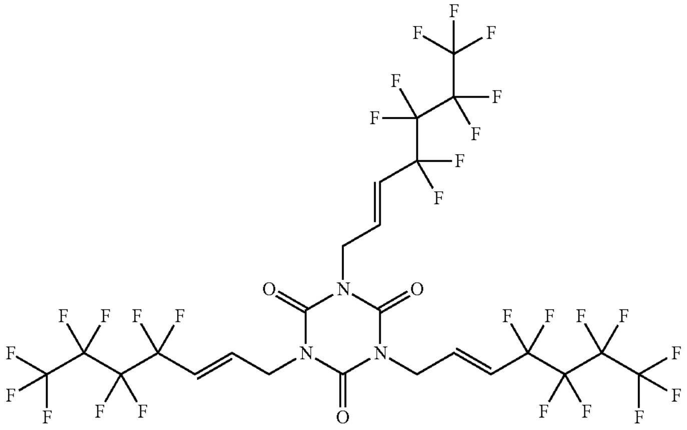
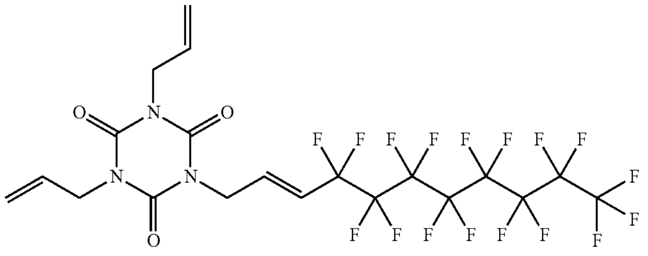
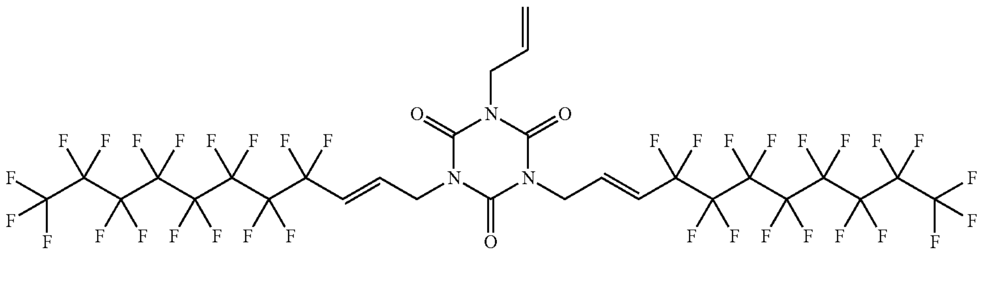

-continued
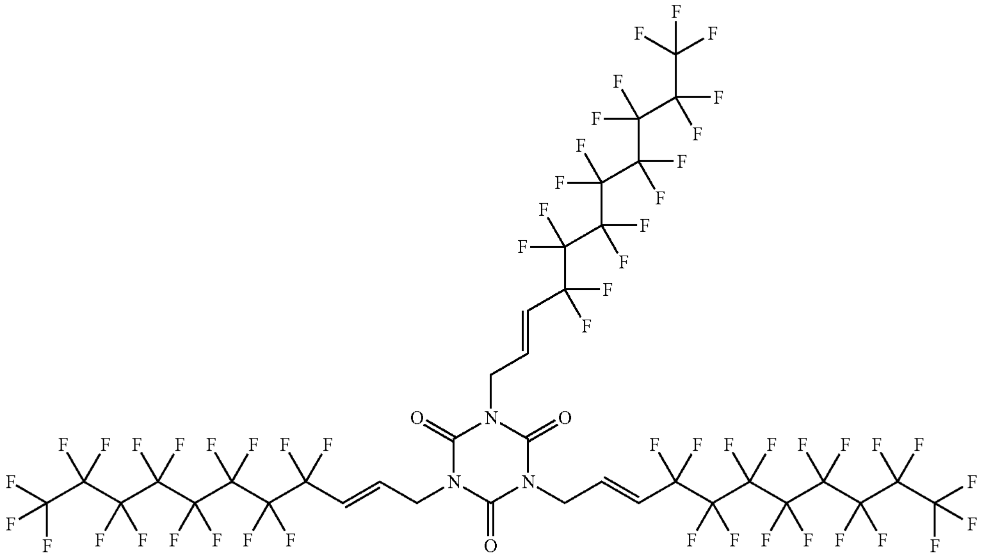
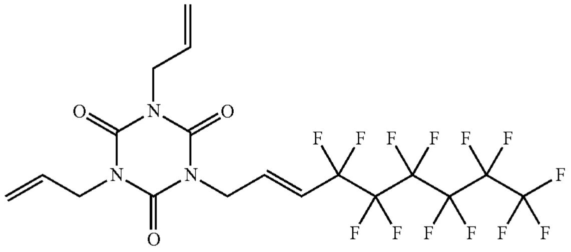
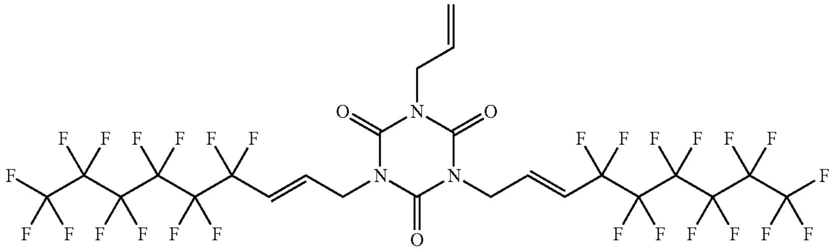
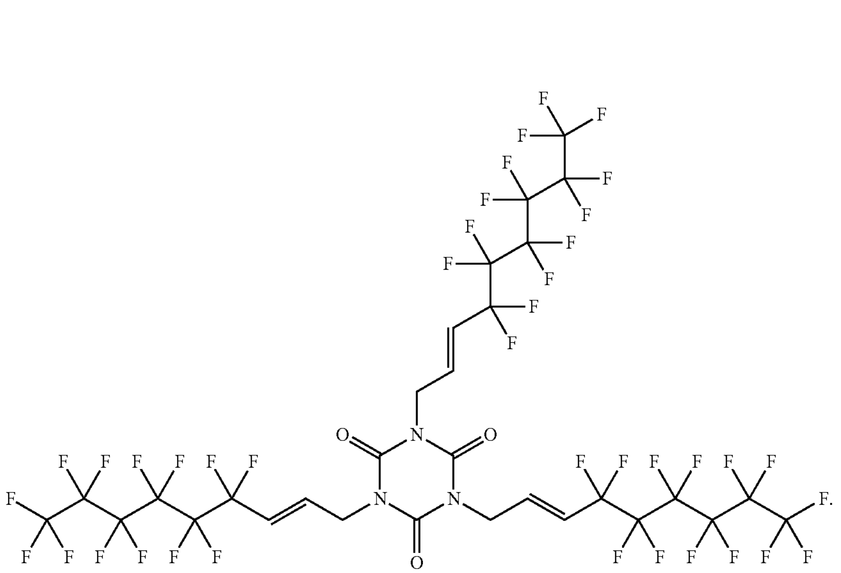

5. A method for preparing a compound of Chemical Formula 1, the method comprising:

(s1) putting triallyl isocyanurate, $C_nF_{2n+1}X4$, a first base, and a first solvent into a container to prepare a mixture and stirring the mixture under nitrogen gas;

(s2) adding a radical initiator thereto and stirring thereof; and (s3) adding a second solvent and a second base thereto to prepare the compound,

[Chemical Formula 1]

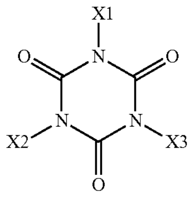

wherein, in the Step (s1)

at least one of X1 to X3 is

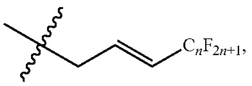

and the others are an allyl group, n is an integer from 1 to 20, and

X4 is a halogen group.

6. A mixture comprising two or more of the compounds of claim 1.

* * * * *